United States Patent [19]
Keyer et al.

[11] Patent Number: 6,090,926
[45] Date of Patent: Jul. 18, 2000

[54] POWDERY, SOLID RARE EARTH CARBOXYLATES WITH IMPROVED SOLUBILITY IN ALIPHATIC SOLVENTS WHICH ARE HIGHLY ACTIVE CATALYSTS IN ZIEGLER-NATTA SYSTEMS

[75] Inventors: Julie Lynn Shreeve Keyer, East Windsor; Kenan Yunlu, Princeton, both of N.J.; Anne Nadine Forgeron, Bedford, Canada; Jean-Pierre Cuif, LaRochelle, France; Anne-Gaelle Morin, Plainsboro, N.J.

[73] Assignee: Rhodia Rare Earths Inc., Shelton, Conn.

[21] Appl. No.: 09/322,684

[22] Filed: May 28, 1999

Related U.S. Application Data

[60] Provisional application No. 60/088,266, Jun. 5, 1998.
[51] Int. Cl.$^7$ ....................................................... C07F 5/00
[52] U.S. Cl. ................................................................ 534/16
[58] Field of Search ................................................. 534/16

[56] References Cited

U.S. PATENT DOCUMENTS

| | | | |
|---|---|---|---|
| 5,017,539 | 5/1991 | Jenkins et al. | 502/102 |
| 5,220,045 | 6/1993 | Knauf et al. | 556/55 |
| 5,360,898 | 11/1994 | Jordaan et al. | 534/16 |
| 5,449,387 | 9/1995 | Hawkins et al. | 44/364 |
| 5,610,114 | 3/1997 | Robert et al. | 502/115 |
| 5,731,381 | 3/1998 | Apecetche et al. | 526/83 |
| 5,783,676 | 7/1998 | Yunlu | 534/16 X |

FOREIGN PATENT DOCUMENTS

| | | |
|---|---|---|
| 0 577 456 A1 | 6/1996 | European Pat. Off. . |
| 97/36850 | 10/1997 | WIPO . |

OTHER PUBLICATIONS

Patent Abstracts of Japan, Publication No. 61176554, Published Aug. 8, 1986, Applicant: Daiichi Eng KK, "Production of Neodymium Octanoate".

Primary Examiner—Fiona T. Powers
Attorney, Agent, or Firm—Katherine L. Carleton

[57] ABSTRACT

Rare earth carboxylates in solid form are prepared or treated with a solubilizing agent to improve the solids solubility in aliphatic solvents. Other methods, such as treatment of the aliphatic solvent, to improve the solubility of solid rare earth carboxylates in aliphatic solvents are also described. Solubilizing agents identified for use include, but are not limited to, carboxylic acids, poly-acids, glycols, alcohols and mixtures thereof. These processes and treatments are particularly useful in regard to solid rare earth versatate, rare earth neodecanoate, rare earth octanoate, rare earth 2-ethyl hexanoate and rare earth naphthenate compositions.

17 Claims, No Drawings

POWDERY, SOLID RARE EARTH CARBOXYLATES WITH IMPROVED SOLUBILITY IN ALIPHATIC SOLVENTS WHICH ARE HIGHLY ACTIVE CATALYSTS IN ZIEGLER-NATTA SYSTEMS

This application claims benefit to U.S. provisional application 60/088,266 filed Jun. 5, 1998.

TECHNICAL FIELD

Rare earth carboxylates in solid form and exhibiting increased solubility in aliphatic solvents are provided, preferably for use in Ziegler-Natta polymerization.

BACKGROUND OF THE INVENTION

The solubility of rare earth carboxylates may be directly related to their catalytic activity in Ziegler-Natta polymerization (homogeneous polymerization) reactions of butadiene, isoprene, and other olefins. Solubility of the solid is measured as the amount of a solid which is dissolved at a given concentration, and can be measured by the transmittance of light through the solution.

The cloudiness produced by the presence of undissolved particles in the solution is measured by the transmittance of light (about 420 nm) through the solution. If there is a quantity of solids remaining undissolved in the solution, it is difficult for light to pass through. As the solid is dissolved in the solution, more light passes through, giving a higher percent transmittance. A solid being approximately completely soluble will allow 100% transmittance of light on the maximum transmittance of light through the solvent.

Improvement of solubility can also include the ability to make more concentrated solutions of rare earth carboxylates. An object of the present invention, is to make, by dissolving the improved solid rare earth carboxylates, a more concentrated solution in comparison to concentrated solutions made by dissolving the original (commercially available) solid rare earth carboxylates.

In this invention, the preparation of powdery, solid rare earth carboxylates which are highly soluble in an aliphatic solvent is described. It is theorized that by the use of other ligands in the place of some of the carboxylate ligands, a powdery solid which is highly soluble in an aliphatic solvent and is also a highly active catalyst for the polymerization of butadiene, isoprene, and mixtures thereof is formed. Also a new method to dissolve solid rare earth carboxylates in an aliphatic solvent using carboxylic acids and other solubilizing agents is described.

Solid rare earth carboxylates with branched long-chain ligands (e.g. rare earth versatate, rare earth neodecanoate, rare earth octanoate, rare earth 2-ethyl hexanoate, rare earth naphthenate and mixtures thereof) can be produced by a variety of methods including solid-state methods, aqueous precipitation, and solvent evaporation. Improved methods including aqueous precipitation and improved solvent evaporation methods provide solid rare earth carboxylates which are powdery and free-flowing. Improved methods are described in U.S. Pat. No. 5,783,676, entitled "Synthesis of Solid, Powdery Rare Earth Carboxylates by a Precipitation Method," Ser. No. 08/623,722, issued Jul. 21, 1998, and in U.S. patent application entitled, "Preparation of Solid, Powdery Rare Earth Carboxylates by Evaporation," Ser. No. 60/040,327, both of which are incorporated herein in their entirety.

One difficulty that has been faced with solid rare earth carboxylates is that the solids are frequently not soluble in organic solvents at as high of concentration as can be obtained from the liquid form. An object of the present invention is to provide a solution to this problem.

Unless otherwise stated, all parts, ratios or percents are by weight.

As used herein, the terms "rare earth carboxylate(s)," "aliphatic solvent(s)," "carboxylic acid(s)," "rare earth salt(s)" "precursor(s)," "reagent(s)," and "solubilizing agent(s)" shall encompass the singular and plural, as well as, to encompass mixtures of the respective compounds.

As used herein, the terms "precursor(s)" and "reagent(s)" mean the components mixed, added, reacted or otherwise combined to form a composition, compound, solution or the like. For example, as used herein precursors or reagents of a carboxylate salt solution can include, but are not limited to, carboxylic acid, base and the reaction medium, e.g., water.

"Comprising" as used herein, means various components can be conjointly employed. Accordingly, the terms "consisting essentially of" and "consisting of" are embodied in the term "comprising."

BRIEF DESCRIPTION OF THE INVENTION

In the scope of this invention, it is theorized that the modification or replacement of a small amount of the carboxylate ligand in a solid rare earth carboxylate (versatate, neodecanoate, 2-ethyl hexanoate, or naphthenate) has been discovered to improve the solubility of said solid in an aliphatic solvent (linear, cyclic, and branched aliphatic solvents including, but not limited to, hexanes, cyclohexane, pentane, heptane, octane, cyclopentane, methylcyclopentane and mixtures thereof). Thus the addition of a solubilizing agent: to the reaction to produce the solid; to the solvent prior to, concurrently with or after the addition of the solid to the solvent; to the solid by impregnation and/or washing; or any combination thereof; can improve the solubility and provide increased concentrations. In one embodiment, the soluble solid produced is a highly active catalyst for the polymerization of butadiene, providing high cis-polybutadiene.

DETAILED DESCRIPTION OF THE INVENTION

Solubilizing agents which improve the solubility of rare earth carboxylates include carboxylic acids (e.g., straight, branched or cyclic; substituted (mono- or poly-) or unsaturated; and saturated) particularly, carboxylic acids of the general formula HOC(O)R, where R is H or a linear or branched aliphatic group containing approximately 1 to 32, preferably 1 to 20, carbon atoms or may be poly-acids (containing more than one carboxylate group) or contain alcohols or other functional groups. These solubilizing agents include, but are not limited to, formic acid, acetic acid, propanoic acid, butyric acid, valeric acid, hexanoic acid, heptanoic acid, octanoic acid (caprylic acid), decanoic acid, lauric acid, trimethyl acetic acid, 2, 2-dimethylbutyric acid, tert-butylacetic acid, 2-propylpentanoic acid, 2-ethylhexanoic acid, naphthenic acid, versatic acid, adipic acid, 3-methyl adipic acid, lactic acid, diglycolic acid, cyclohexanecarboxylic acid, cyclohexanepropanoic acid and corresponding bases of the solubilizing agents and mixtures thereof. Also, mono- and di-carboxylic acids are suitable for use, particularly mono- and di-carboxylic acids of the general formula: $R_3$—C(O)OH where R is H or an alkyl group having from about 1 to about 15 carbon atoms.

Also included are poly-acids such as EDTA (ethylenediaminetetraacetic acid) and derivatives therein including H₃HEDTA, diethylenetriaminepentaacetic acid (H₅DTPA), diethylhexylphosphoric acid (D₂EHPA), and nitrilotriacetic acid; alcohols, including, but not limited to, alcohols of the general formula HOR,' dialcohols of the general formula HOR'OH, where R' is a linear or branched aliphatic group containing approximately 1 to 20 carbon atoms, and polyhydric alcohols such as trihydric alcohols, e.g., glycerol; glycols such as methylene glycol, ethylene glycol, propylene glycol, diethylene glycol, dipropylene glycol, ethylene glycol dimethyl ether, and di (ethylene glycol) dibutyl ether; glycol derivatives such as ethylene carbonate (glycol carbonate); trialkylphosphates of the general formula (RO)₃P(O), where R is a linear or branched aliphatic group containing approximately 1 to 32, preferably 1 to 20, carbon atoms or more than one carboxylate group or alcohols (—OH) or other functional groups, such as tributylphosphate (C₄H₉O)₃P(O); and mixtures thereof Additional solubilizing agents are succinic anhydrides; dimethylsulfones; formamides; amines including, but not limited to, ethanolamines (MEA); furans; ethers; pyridines; silanes; ketones; and mixtures thereof. The solubilizing agents can be used in approximately from about 0.5 to about 50 mole percent, preferably approximately from about 0.5 to about 8 mole percent ratio to the other carboxylate ligands.

Carboxylic acids are well known and described in, for example Kirk-Othmer Encyclopedia of Chemical Technology, fourth edition, John Wiley & Son, New York, 1993, vol. 5, pp. 147–192, which is incorporated herein by reference. As used herein "neodecanoic acid" and "versatic acid" are mixtures of predominately branched carboxylic acids, generally the majority being about 10 carbon atoms.

To enhance the solubility of rare earth carboxylates in aliphatic solvents, one method is to add the solubilizing agent to the reaction to produce the rare earth carboxylate. Any reaction can be utilized. This can be done by adding to one or more of the precursors (reagents). The most common reaction comprises mixing a carboxylate salt solution and a rare earth solution. Thus, the solubilizing agent can be mixed with the carboxylate salt solution and the rare earth salt solution. The solubilizing agent can also be added to one or both of the carboxylate salt solutions and rare earth salt solution prior to reaction. Preferably, the solubilizing agent is added to a precursor (e.g., carboxylic acid) of the carboxylate salt solution.

As stated previously, the solubilizing agent can be added to any reaction for making a rare earth carboxylate. For illustrative purposes a precipitation reaction is generally described herein utilizing a carboxylate salt solution and a rare earth salt solution.

In accordance with one embodiment the present invention, a solubilizing agent is typically added to the carboxylic acid, before formation of the sodium, potassium, lithium or ammonium salt which is reacted with the rare earth salt to form a solution of rare earth carboxylate. This solution is then dried giving the powdery, solid rare earth carboxylate.

The carboxylate solution is preferably prepared by reaction of the carboxylic acid (preferably versatic acid, neodecanoic acid, octanoic acid, 2-ethylhexanoic acid, and naphthenic acid) or mixtures thereof with a base which is an alkali metal, alkaline earth metal or ammonium (preferably tetra (lower alkyl) ammonium) oxide, hydroxide, carbonate or hydrogen carbonate. Preferably, the solubilizing agent is added to the carboxylic acid before reaction with the base.

The base suitable for reaction with the carboxylic acid is preferably a hydroxide of an alkali metal of Group I, preferably lithium, sodium or potassium. Most preferably the base is a hydroxide of sodium. Other bases suitable for use include: sodium hydroxide, lithium hydroxide, potassium hydroxide, ammonium hydroxide, tetrabutyl ammonium hydroxide, tetra methyl ammonium hydroxide, and tetra ethyl ammonium hydroxide.

The reaction of the carboxylic acid and the base preferably occurs in the presence of water to form the carboxylate salt solution. Thus, water is a preferred reaction medium.

The preferred solubilizing agents for addition to one or more of the precursors/reagents (e.g., carboxylic acid, base, and/or reaction medium) of the carboxylate salt solution, preferably are selected from the group consisting of carboxylic acids, bases of carboxylic acids, alcohols and mixtures thereof. More preferably, these solubilizing agents are added to the carboxylic acid. Preferred solubilizing agents for addition to the carboxylic acid are selected from the group consisting of:

a) alcohols of the general formula HOR', where R' is a linear or branched aliphatic group having from about 1 to 20 carbons;

b) dialcohols of the general formula HOR'OH, where R' is a linear or branched aliphatic group having from about 1 to 20 carbons;

c) polyhydric alcohols;

d) carboxylic acids selected from the group consisting of: formic acid, acetic acid, propanoic acid, butyric acid, caprylic acid, valeric acid, hexanoic acid, heptanoic acid, octanoic acid, decanoic acid, lauric acid, trimethyl acetic acid, 2-2-dimethylbutyric acid, tert-butylacetic acid, 2-propylpentanoic acid, 2-ethylhexanoic acid, naphthenic acid, versatic acid, adipic acid, 3-methyl adipic acid, lactic acid, diglycolic acid, cyclohexanecarboxylic acid, cyclohexanepropanoic acid, and mixtures thereof;

e) one or more corresponding bases of the carboxylic acids selected from the group consisting of: formic acid, acetic acid, propanoic acid, butyric acid, caprylic acid, valeric acid, hexanoic acid, heptanoic acid, octanoic acid, decanoic acid, lauric acid, trimethyl acetic acid, 2-2-dimethylbutyric acid, tert-butylacetic acid, 2-propylpentanoic acid, 2-ethylhexanoic acid, naphthenic acid, versatic acid, adipic acid, 3-methyl adipic acid, lactic acid, diglycolic acid, cyclohexanecarboxylic acid, cyclohexanepropanoic acid, and mixtures thereof; and f) mixtures thereof.

The most preferred solubilizing agents for addition to the carboxylic acid are selected from the group consisting of: propanoic acid, butyric acid, caprylic acid and mixtures thereof.

The carboxylate salt solution is then preferably reacted with a rare earth nitrate (RE(NO₃)₃), chloride, oxide or the like to produce the rare earth carboxylate in the presence of an organic solvent, e.g. an aliphatic solvent, to form a rare earth carboxylate solution. Any rare earth water soluble salt or mixture thereof can be utilized, such as rare earth chlorides and the like. The rare earth salts, preferably nitrates, suitable for use are the salts of group III B of the periodic table (lanthanide series). Suitable rare earth salts, preferably nitrates, are, for example, the salts of lanthanum, cerium, praseodymium, neodymium, promethium, samarium, europium, gadolinium, terbium, dysprosium, holmium, yttrium, erbium, thulium, ytterbium and lutetium. Preferred for use are the nitrates of neodymium, lanthanum, praseodymium and cerium (preferably Ce III). Most preferred are the nitrates of neodymium.

Aliphatic solvents are known in the art. Aliphatic solvents can be linear, cyclic and/or branched aliphatic solvents including, but not limited to, hexanes, cyclohexane, pentane, neptane, octane, cyclopentane, methylcyclopentane, and mixtures thereof. The reaction of the carboxylate salt solution and the rare earth salt (or a rare earth salt solution) generally produces a solution with an aqueous and organic layer. Generally, in such a process the aqueous layer is removed and the organic layer is washed and dried, preferably under vacuum, to produce a rare earth carboxylate solid.

Thus, the solid rare earth carboxylates can be produced by a process comprising the step of: adding to one or more reagents for a reaction to produce a rare earth carboxylate a solubilizing agent, preferably selected from the group consisting of: formic acid, acetic acid, propanoic acid, butyric acid, valeric acid, hexanoic acid, heptanoic acid, octanoic acid (caprylic acid), decanoic acid, lauric acid, trimethyl acetic acid, 2, 2-dimethylbutyric acid, tert-butylacetic acid, 2-propylpentanoic acid, 2-ethylhexanoic acid, naphthenic acid, versatic acid, adipic acid, 3-methyl adipic acid, lactic acid, diglycolic acid, cyclohexanecarboxylic acid, cyclohexanepropanoic acid, poly-acids (preferably ethylenediaminetetraacitic acid $H_3HEDTA$, diethylenetriaminepentaacetic acid ($H_5DTPA$), diethylhexylphosphoric acid ($D_2EHPA$), and nitilotriacetic acid), alcohols, polyhydric alcohols, glycols, glycol derivatives, trialkylphosphates (preferably tributylphosphate $(C_4H_9O)_3P(O)$), succinic anhydrides, dimethylsulfones, formamides, amines, furans, ethers, pyridines, silanes, ketones, and mixtures thereof.

In a reaction to produce a solid rare earth carboxylate, the solubilizing agents of the present invention can be added after the formation of the rare earth carboxylate solution, yet before drying.

Another preferred reaction process is the reaction of a carboxylic acid and a rare earth oxide to form a rare earth carboxylate. An embodiment of the present invention for preparing a solid rare earth carboxylate comprises the step of: mixing a solubilizing agent, preferably a carboxylic acid, an alcohol or mixtures thereof, with a carboxylic acid to form a mixture and dissolution of a rare earth oxide by adding the mixture to the rare earth oxide to form a rare earth carboxylate. Preferably, the reaction of the carboxylic acid mixture and rare earth oxide occurs in an organic solvent medium.

Before, rare earth carboxylate solids (versatate, neodecanoate, octanoate, 2-ethyl hexanoate, or naphthenate) were difficult or impossible to dissolve in straight aliphatic solvents yet could be somewhat dissolved in cyclo-aliphatic solvents. Solid rare earth carboxylates prepared in accordance with the present invention are easily dissolved in all types of aliphatic solvents and demonstrate improved solubility in these solvents. On a mole percent basis, the solubilizing agents are added in the range of from about 1 to about 20 mole percent, preferably from about 1 to about 10 mole percent, more preferably from about 1 to about 5 mole percent and most preferably from about 2 to about 5 mole percent.

Another method for improving the solubility of solid rare earth carboxylates (versatate, neodecanoate, octanoic, 2-ethyl hexanoate, or naphthenate) in aliphatic solvents involves the addition of the solubilizing agent to the rare earth carboxylate solid, or to the aliphatic solvent prior to, concurrently with, and/or after adding the solid to the solvent, or both. One embodiment is the addition of a solubilizing agent to the aliphatic solvent prior to or concurrently with the addition of the solid rare earth carboxylate. If added after the addition of the rare earth carboxylate, good agitation is recommended. Preferably, the solubilizing agent is added prior to or concurrently with the addition of the solid rare earth carboxylate to the solvent. In this method, the solubilizing agent is preferably not utilized during the formation of the solid rare earth carboxylate. Solubilizing agents are added to the aliphatic solvent. Any of the solubilizing agents described herein can be used. Preferably, these solubilizing agents can be added to the solvent in approximately 0.1 to 25 weight percent, preferably from about 0.1 to 5 weight percent.

The solubilizing agent can also be introduced to the solid by impregnation of the solid with the solubilizing agent (preferably during grinding) and/or by washing the solid with the solubilizing agent. Such treatment will improve the solubility of the solid in aliphatic solvents.

Finally, any combination of these methods can be utilized. The solubilizing agent can be added to the reaction to produce the solid (preferably by addition to one or more of the reagents/precursors); prior to, concurrently with, or after the addition of the solid to the aliphatic solvent; to the solid by impregnation and/or washing; or any combination thereof.

The following examples are provided to better describe and define the processes and products of the present invention without limiting the scope thereof. They are for illustrative purposes and it is realized that changes or variations may be made which do not materially alter the composition or process and are still considered to fall within the scope of the invention.

EXAMPLES

Example 1

Approximately 1 molar equivalent of aqueous NaOH is combined with neodecanoic acid until the pH is approximately 9, forming an aqueous solution of a salt of the carboxylic acid. The total volume of the solution is doubled by addition of hexanes. Nd nitrate is added to the previously formed mixture until the pH of the aqueous phase is about 6.5. The organic layer is decanted and washed with water to remove all nitrates, to give a solution of Nd neodecanoate, and the free acid content is adjusted if necessary. This solution is then dried under vacuum at 80° C. to form a powdery solid. The above prepared solid is placed in dry hexanes in a concentration corresponding to approximately 4 weight percent Nd (ca. 0.2 M). The transmittance of light through this solution is approximately 0.6% after approximately 1 hour and 24 hours.

Example 2

A solid is prepared as described in Example 1, however a mixture of approximately 4 molar percent propanoic acid and approximately 96 molar percent neodecanoic acid is used in place of the neodecanoic acid. The above prepared solid is placed in dry hexanes in a concentration corresponding to 4 weight percent Nd (ca. 0.2 M). The transmittance of light through this solution is approximately 100% after approximately 1 hour and 24 hours.

Example 3

A solid is prepared as described in Example 2. The above prepared solid is placed in dry hexanes in a concentration corresponding to 9 weight percent Nd (ca. 0.4 M). The transmittance of light through this solution is approximately 100% after approximately 1 hour and 24 hours.

Example 4

A solid is prepared as described in Example 1, however a mixture of approximately 5 molar percent of cyclohexane carboxylic acid and approximately 95 molar percent neodecanoic acid is used in place of the neodecanoic acid. The above prepared solid is placed in dry hexanes in a concentration corresponding to 4 weight percent Nd (ca. 0.2 M). The transmittance of light through this solution is approximately 100% after approximately 1 hour and 24 hours.

Example 5

A solid is prepared as described in Example 1. The above prepared solid is placed in dry hexanes which contain approximately 3 molar percent propanoic acid in a concentration corresponding to 4 weight percent Nd (ca. 0.2 M). The transmittance of light through this solution is approximately 100% after approximately 1 hour and 24 hours.

Example 6

A solid prepared according to Example 1 is dissolved in cyclohexane and added to a reactor containing cyclohexane, butadiene and di-isobutyl aluminum hydride. Diethyl aluminum chloride is then added. The molar ratio H/Nd/Cl is approximately 40/1/3. The polymerization is carried out at a concentration of about 0.2 mmol Nd per 100 g BD for about 2 hours at about 70° C. The polybutadiene obtained after removal of solvent corresponds to approximately 87%, with a cis content of approximately 98%.

Example 7

A solid prepared according to Example 2 is dissolved in cyclohexane and added to a reactor containing cyclohexane, butadiene and di-isobutyl aluminum hydride. Diethyl aluminum chloride is then added. The mole ratio H/Nd/Cl is approximately 401113. The polymerization is carried out at a concentration of about 0.2 umnol Nd per 100 g BD for about 2 hours at about 70° C. The polybutadiene obtained after removal of solvent corresponds to approximately 89%, with a cis content of approximately 98%.

What is claimed is:

1. A process for making a solid rare earth carboxylate product comprising the steps of: adding to one or more reagents, prior to or concurrently with reaction of said reagents in a reaction solvent to form a rare earth carboxylate, a solubilizing agent selected from the group consisting of:

a) carboxylic acids,
   b) corresponding bases of carboxylic acids,
   c) poly-acids,
   d) glycols,
   e) glycol derivatives,
   f) trialkylphosphates,
   g) succinic anhydrides,
   h) dimethylsulfones,
   i) formamides,
   j) amines,
   k) furans,
   l) ethers,
   m) pyridines,
   n) silanes,
   o) ketones, and
   p) mixtures thereof;

and removing the reaction solvent to provide the solid rare earth carboxylate product.

2. A process according to claim 1, wherein said reagents are selected from the group consisting of: carboxylic acids, bases, reaction medium, carboxylate salt solutions, rare earth salt solutions, and rare earth salts, and said solubilizing agent is selected from the group consisting of: carboxylic acids, glycols, formamides, and mixtures thereof.

3. A process according to claim 2, wherein said solubilizing agent is selected from the group consisting of: formic acid, acetic acid, propanoic acid, butyric acid, valeric acid, hexanoic acid, heptanoic acid, octanoic acid, decanoic acid, lauric acid, trimethyl acetic acid, 2-2-dimethylbutyric acid, tert-butylacetic acid, 2-propylpentanoic acid, 2-ethylhexanoic acid, naphthenic acid, versatic acid, adipic acid, 3-methyl adipic acid, lactic acid, diglycolic acid, cyclohexanecarboxylic acid, cyclohexanepropanoic acid, methylene glycol, ethylene glycol, propylene glycol, diethylene glycol, dipropylene glycol, ethylene glycol dimethyl ether, di (ethylene glycol) dibutyl ether, formamide, and mixtures thereof; said rare earth salt is selected from the group consisting of: rare earth nitrates, rare earth oxides, rare earth chlorides and mixtures thereof; and said carboxylic acids are selected from the group consisting of: versatic acid, neodeconoic acid, octanoic acid, 2-ethylhenanoic acid, naphthenic acid and mixtures thereof.

4. A process according to claim 3, wherein said solubilizing agent is selected from the group consisting of: propanoic acid, butyric acid, octanoic acid, ethylene glycol, formamide and mixtures thereof.

5. A precipitation process for making a solid rare earth carboxylate product comprising the steps of:

a) adding to a carboxylic acid a solubilizing agent selected from the group consisting of: carboxylic acids, bases of carboxylic acids, alcohols and mixtures thereof, to form a mixture;
   b) mixing the mixture with a base to form a carboxylate salt solution;
   c) mixing the carboxylate salt solution with a rare earth salt solution to form a rare earth carboxylate solution, and
   d) drying the rare earth carboxylate solution to form the solid rare earth carboxylate product.

6. The process according to claim 5, wherein said solubilizing agent is selected from the group consisting of:

a) alcohols of the general formula HOR', where R' is a linear or branched aliphatic group having from 1 to 20 carbon;
   b) dialcohols of the general formula HOR'OH, where R' is a linear or branched aliphatic group having from 1 to 20 carbon;
   c) polyhydric alcohols;
   d) carboxylic acids selected from the group consisting of: formic acid, acetic acid, propanoic acid, butyric acid, caprylic acid, valeric acid, hexanoic acid, heptanoic acid, octanoic acid, decanoic acid, lauric acid, trimethyl acetic acid, 2-2-dimethylbutyric acid, tert-butylacetic acid, 2-propylpentanoic acid, 2-ethylhexanoic acid, naphthenic acid, versatic acid, adipic acid, 3-methyl adipic acid, lactic acid, diglycolic acid, cyclohexanecarboxylic acid, cyclohexanepropanoic acid, and mixtures thereof;
   e) one or more corresponding bases of the carboxylic acids selected from the group consisting of: formic acid, acetic acid, propanoic acid, butyric acid, caprylic acid, valeric acid, hexanoic acid, heptanoic acid, octanoic acid, decanoic acid, lauric acid, trimethyl acetic acid, 2-2-dimethylbutyric acid, tert-butylacetic acid, 2-propylpentanoic acid, 2-ethylhexanoic acid, naphthenic acid, versatic acid, adipic acid, 3-methyl adipic acid, lactic acid, diglycolic acid, cyclohexanecarboxylic acid, cyclohexanepropanoic acid, and mixtures thereof; and f) mixtures thereof.

7. The process according to claim 6, wherein said solubilizing agent is selected from the group consisting of: propanoic acid, butyric acid, caprylic acid and mixtures thereof.

8. The process according to claim 1 or 5, comprising the additional steps of:

i) washing, ii) impregnating, or iii) washing and impregnating, the solid rare earth carboxylate product with a solubilizing agent selected from the group consisting of:

| | | |
|---|---|---|
| a) | carboxylic acids, | |
| b) | corresponding bases of carboxylic acids, | |
| c) | poly-acids, | |
| d) | glycols, | |
| e) | glycol derivatives, | |
| f) | trialkylphosphates, | |
| g) | succinic anhydrides, | |
| h) | dimethylsulfones, | |
| i) | formamides, | |
| j) | amines | |
| k) | furans, | |
| l) | ethers, | |
| m) | pyridines, | |
| n) | silanes, | |
| o) | ketones, and | |
| p) | mixtures thereof. | |

9. A process for making a solid rare earth carboxylate product comprising the steps of: mixing a solubilizing agent with a carboxylic acid to form a mixture; dissolution of a rare earth oxide by adding the mixture to the rare earth oxide to form a rare earth carboxylate; and drying to form the solid rare earth carboxylate product;

wherein said solubilizing agent is selected from the group consisting of:

| | | |
|---|---|---|
| a) | carboxylic acids, | |
| b) | alcohols, | |
| c) | corresponding bases of carboxylic acids, | |
| d) | poly-acids, | |
| e) | glycols, | |
| f) | glycol derivatives, | |
| g) | trialkylphosphates, | |
| h) | succinic anhydrides, | |
| i) | dimethylsulfones, | |
| j) | formamides, | |
| k) | amines, | |
| l) | furans, | |
| m) | ethers, | |
| n) | pyridines, | |
| o) | silanes, | |
| p) | ketones, and | |
| q) | mixtures thereof. | |

10. A process according to claim 9, wherein:

a) said solubilizing agent is selected from the group consisting of: carboxylic acids, bases of carboxylic acids, alcohols and mixtures thereof; and b) said carboxylic acid is selected from the group consisting of: versatic acid, neodecanoic acid, octanoic acid, 2-ethylhexanoic acid, naphthenic acid and mixtures thereof.

11. A method for improving the solubility of a solid rare earth carboxylate in an aliphatic solvent comprising the steps of: adding a solubilizing agent to the aliphatic solvent prior to, concurrently with, or after addition of the solid rare earth carboxylate to the aliphatic solvent; wherein said solubilizing agent is selected from the group consisting of:

| | | |
|---|---|---|
| a) | bases of carboxylic acids, | |
| b) | poly-acids, | |
| c) | glycols, | |
| d) | glycol derivatives, | |
| e) | trialkylphosphates, | |
| f) | succinic anhydrides, | |
| g) | dimethylsulfones, | |
| h) | formamides, | |
| i) | furans, | |
| j) | pyridines, | |
| k) | silanes, | |
| l) | ketones, and | |
| m) | mixtures thereof. | |

12. A method according to claim 11, wherein a) said solubilizing agent is selected from the group consisting of: bases of carboxylic acids, glycols, formamides, and mixtures thereof;

b) said solid rare earth carboxylate is selected from the group consisting of: rare earth versatate, rare earth neodecanoate, rare earth octanoate, rare earth 2-ethyl hexanoate, rare earth naphthenate and mixtures thereof; and c) said aliphatic solvent is selected from the group consisting of: hexanes, cyclohexane, pentane, heptane, octane, cyclopentone, methylcyclopentane and mixtures thereof.

13. A method according to claim 11, wherein said solubilizing agent is added prior to or concurrently with said solid rare earth carboxylate.

14. A method for improving the solubility of a solid rare earth carboxylate in an aliphatic solvent comprising the steps of: adding a solubilizing agent to the aliphatic solvent prior to or concurrently with addition of the solid rare earth carboxylate to the aliphatic solvent; wherein said solubilizing agent is selected from the group consisting of: formic acid, acetic acid, propanoic acid, butyric acid, valeric acid, hexanoic acid, heptanoic acid, octanoic acid, decanoic acid, lauric acid, trimethyl acetic acid, 2-2-dimethylbutyric acid, tert-butylacetic acid, 2-propylpentanoic acid, 2-ethylhexanoic acid, naphthenic acid, adipic acid, 3-methyl adipic acid, lactic acid, diglycolic acid, cyclohexanecarboxylic acid, cyclohexanepropanoic acid, methylene glycol, ethylene glycol, propylene glycol, diethylene glycol, dipropylene glycol, ethylene glycol dimethyl ether, di (ethylene glycol) dibutyl ether, formamide, and mixtures thereof.

15. A method according to claim 14, wherein said solubilizing agent is selected from the group consisting of: propanoic acid, butyric acid, octanoic acid, ethylene glycol, formamide and mixtures thereof.

16. A method for improving the solubility of a solid rare earth carboxylate in an aliphatic solvent comprising the steps of:

| | | |
|---|---|---|
| i) | washing, | |
| ii) | impregnating, or | |
| iii) | washing and impregnating, | | a solid rare earth carboxylate with a solubilizing agent selected from the group consisting of:

a) carboxylic acids,
b) corresponding bases of carboxylic acids,
c) poly-acids,
d) glycols,
e) glycol derivatives,
f) trialkylphosphates,
g) succinic anhydrides,
h) dimethylsulfones,
i) formamides,
j) amines,
k) furans,
l) ethers,
m) pyridines,
n) silanes,
o) ketones, and
p) mixtures thereof.

17. A method according to claim 16, wherein a) said solubilizing agent is selected from the group consisting of: formic acid, acetic acid, propanoic acid, butyric acid, valeric acid, hexanoic acid, heptanoic acid, octanoic acid, decanoic acid, lauric acid, trimethyl acetic acid, 2-2-dimethylbutyric acid, tert-butylacetic acid, 2-propylpenitanoic acid, 2-ethylhexanoic acid, naphthenic acid, versatic acid, adipic acid, 3-methyl adipic acid, lactic acid, diglycolic acid, cyclohexanecarboxylic acid, cyclohexanepropanoic acid, methylene glycol, ethylene glycol, propylene glycol, diethylene glycol, dipropylene glycol, ethylene glycol dimethyl ether, di (ethylene glycol) dibutyl ether, formamide, and mixtures thereof; and b) said solid rare earth carboxylate is selected from the group consisting of: rare earth versatate, rare earth neodeconate, rare earth 2-ethylhexonoate, rare earth naphthenate and mixtures thereof.

* * * * *